United States Patent [19]
Schroeder et al.

[11] Patent Number: 5,664,563
[45] Date of Patent: Sep. 9, 1997

[54] PNEUMATIC SYSTEM

[75] Inventors: Gary Schroeder, North Londonderry, N.H.; James W. Biondi, North Haven, Conn.; Douglas M. Johnston, Winchester, Mass.

[73] Assignee: Cardiopulmonary Corporation, Milford, Conn.

[21] Appl. No.: 352,658

[22] Filed: Dec. 9, 1994

[51] Int. Cl.$^6$ .................................................. A61M 16/00
[52] U.S. Cl. .................... 128/204.25; 128/204.24; 128/204.28; 128/205.13; 128/205.14; 128/205.24
[58] Field of Search ........................ 128/204.21, 204.22, 128/204.24, 204.25, 204.28, 205.11, 205.12, 205.13, 205.14, 205.17, 205.24, 205.27, 205.28, 205.29, 205.15

[56] References Cited

U.S. PATENT DOCUMENTS

| | | | |
|---|---|---|---|
| 3,303,841 | 2/1967 | Dennis . | |
| 3,741,208 | 6/1973 | Jonsson et al. | 128/145.6 |
| 3,817,246 | 6/1974 | Weigl | 128/145.8 |
| 3,972,327 | 8/1976 | Ernst et al. | 128/145.8 |
| 4,036,253 | 7/1977 | Fegan et al. | 137/556 |
| 4,072,148 | 2/1978 | Munson et al. | 128/205.11 |
| 4,072,241 | 2/1978 | Gravenstein et al. | 128/205.12 |
| 4,155,356 | 5/1979 | Venegas | 128/145.6 |
| 4,163,450 | 8/1979 | Kirk et al. | 128/145.8 |
| 4,164,219 | 8/1979 | Bird | 128/145.8 |
| 4,169,465 | 10/1979 | Walls et al. | 128/719 |
| 4,182,366 | 1/1980 | Boehringer | 137/510 |
| 4,211,221 | 7/1980 | Schwanbom et al. | 128/204.26 |
| 4,256,100 | 3/1981 | Levy et al. | 128/204.21 |
| 4,265,237 | 5/1981 | Schwanbom et al. | 128/204.24 |
| 4,323,064 | 4/1982 | Hoenig et al. | 128/204.21 |
| 4,340,044 | 7/1982 | Levy et al. | 128/204.21 |
| 4,397,306 | 8/1983 | Weisfeldt et al. | 128/28 |
| 4,401,116 | 8/1983 | Fry et al. | 128/205.24 |
| 4,417,573 | 11/1983 | De Vries | 128/204.25 |
| 4,424,806 | 1/1984 | Newman et al. | 128/28 |
| 4,448,058 | 5/1984 | Jaffe et al. | 73/23 |
| 4,448,192 | 5/1984 | Stawitcke et al. | 128/204.26 |
| 4,459,982 | 7/1984 | Fry | 128/204.23 |
| 4,509,359 | 4/1985 | Gedeon et al. | 73/23 |
| 4,509,551 | 4/1985 | Luper | 137/554 |
| 4,527,557 | 7/1985 | DeVries et al. | 128/204.23 |

(List continued on next page.)

FOREIGN PATENT DOCUMENTS

| | | |
|---|---|---|
| 0166305 A2 | 1/1986 | European Pat. Off. . |
| 0281180 A1 | 9/1988 | European Pat. Off. . |
| 0606909 A1 | 7/1994 | European Pat. Off. . |
| 1375718 | 11/1974 | United Kingdom . |
| 1488317 | 10/1977 | United Kingdom . |
| WO90/03820 | 4/1990 | WIPO . |

OTHER PUBLICATIONS

Article "Determination of Pulmonary Parenchymal Tissue Volume and Pulmonary Capillary Blood Flow in Man", Leon Cander, et al., J. Appl. Physiol. 14(4): 541–551 –1959.
Article "Rebreathing Measurements of Pulmonary Hempdynamics", Marvin A. Sackner, et al., Amercan Review of Respiratory Disease, vol. 111, 1975.
Article "Comparison of Lung Diffusing Capacity During Rebreathing and During Slow Exhalation", Charles Felton, et al., Respiration Physiology, pp. 13–22, 1981.
Article "Theoretical Basis of Single Breath Gas Absorption Tests", T.B. Martonen, et al., Journal of Mathematical Biology, pp. 203–220, 1982.

(List continued on next page.)

*Primary Examiner*—V. Millin
*Assistant Examiner*—V. Srivastava
*Attorney, Agent, or Firm*—Testa, Hurwitz & Thibeualt, LLP

[57] ABSTRACT

A pneumatic system is provided for a ventilator is provided for controlling inspired and expired patient gas flow during respiratory therapy. The pneumatic system includes a pneumatic circuit for controlling a supply of one or more selected gases to a patient and a disposable patient breathing circuit for isolating exhaled patient gasses from the pneumatic circuit. The pneumatic circuit includes a dual venturi for assisting compression and expansion of a flexible gas reservoir of the patient breathing circuit.

14 Claims, 7 Drawing Sheets

U.S. PATENT DOCUMENTS

| | | | |
|---|---|---|---|
| 4,546,793 | 10/1985 | Stupecky | 137/554 |
| 4,552,142 | 11/1985 | Hoffman et al. | 128/207.16 |
| 4,573,462 | 3/1986 | Baum | 128/205.12 |
| 4,608,995 | 9/1986 | Linnarsson et al. | 128/713 |
| 4,613,111 | 9/1986 | Paquet et al. | 251/46 |
| 4,632,107 | 12/1986 | Butler | 128/204.24 |
| 4,637,384 | 1/1987 | Schroeder | 128/204.18 |
| 4,637,385 | 1/1987 | Reisz | 128/205.14 |
| 4,646,733 | 3/1987 | Stroh et al. | 128/207.16 |
| 4,676,232 | 6/1987 | Olsson et al. | 128/28 |
| 4,686,974 | 8/1987 | Sato et al. | 128/204.23 |
| 4,702,240 | 10/1987 | Chaoui | 128/204.18 |
| 4,727,871 | 3/1988 | Smargiassi et al. | 128/204.17 |
| 4,747,402 | 5/1988 | Reese et al. | 128/204.21 |
| 4,753,226 | 6/1988 | Zheng et al. | 128/64 |
| 4,838,257 | 6/1989 | Hatch | 128/204.18 |
| 4,840,167 | 6/1989 | Olsson et al. | 128/28 |
| 4,877,023 | 10/1989 | Zalkin | 128/204.21 |
| 4,928,674 | 5/1990 | Halperin et al. | 128/30.2 |
| 5,020,516 | 6/1991 | Biondi et al. | 128/30.2 |
| 5,040,529 | 8/1991 | Zalkin | 128/204.25 |
| 5,315,990 | 5/1994 | Mondry | 128/205.11 |

OTHER PUBLICATIONS

Article "Hemodynamic Effects of Synchronous High-Frequency Jet Ventilation During Acute Hypovolemia" George M. Matuschak, et al., American Physiological Society, pp. 44–53, 1986.

Article "Cardiopulmonary Interaction—The Effects of Negative and Positive Pleural Pressure Changes on Cardiac Output", Michael R. Pinsky, Cardiopulmonary Critical Care, pp. 89–121, 1986.

Article "Rest and Exercise Cardiac Output and Diffusing Capacity Assessed by a Single Slow Exhalation of Methane, Acetylene, and Carbon Monoxide", James E. Ramage, Jr., M.D., et al., Chest, pp. 44–50, Jul. 1987.

Article "Effect of Synchronous Increase in Intrathoracic Pressure on Cardiac Performance During Acute Endotoxemia", Jean–Gilles Guimond, et al., American Physiological Society, pp. 1502–1508, 1990.

Article "Noninvasive Determination of Effective (Nonshunted) Pulmonary Blood Flow in Normal and Injured Lungs", Curt M. Steinhart, MD, et al., Critical Care Medicine, pp. 349–353, 1989.

Article "The Ventilator of the 1900s", Thomas D. East Ph.D., Respiratory Care, Vo. 35, No. 3, pp. 232–240, Mar. 1990.

Article "Observations of Hemodynamics During Human Cardiopulmonary Resuscitation", Nisha Chibber Chandra, MD, et al., Critical Care Medicine, Vo. 18, No. 9, pp. 929–934, 1990.

Article "Hemodynamic Effects of 1:2 ECG–Coupled Jet Ventilation in the Dog", Douglas S. Schulman, et al., Am Rev Respir Dis, pp. 819–825, 1991.

Paper "Ventilation in the Information Age", Warren G. Sanborn, PhD, Presented at Product Opportunities in Critical Care Medicine, May 18, 1989.

Paper "The Next Generation: Ventilation in the 90's", Jim Hitchin, presented at the Advances in Anesthesia Procedures and Products, May 24, 1990.

*Book entitled "Principles and Practice of Mechanical Ventilation", Martin J. Tobin, M.D., McGraw Hill, Inc., 1994.

Brochure "Ventilatory Treatment of Neonates and Infants", G. Noack, M.D., St. Goran's Children's Hospital, Stockholm, Servo Library, English Art. No: 61–42173 E310E, Apr. 1993.

Brochures from Infant Star, Infrasonics, Inc. (not admitted to be prior art).

Article "Pulmonary Perfusion Monitor", Belleville and Wiberg, The Crump Institute for Medical Engineering, University of California, Los Angeles, CA. (not admitted to be prior art).

Servo Ventilator 900C Operating Manual, Siemens (not admitted to be prior art).

Servo Ventilator 300 Service Manual—Preliminary, Siemens (not admitted to be prior art).

VEOLAR Operator's Manual, Hamilton Medical (not admitted to be prior art).

Adult Star Ventilator Operating Instructions (not admitted to be prior art).

Bear 5 Ventilator Manual (not admitted to be prior art).

Puritan Bennett 7200 Series Ventilatory System Operators Manual Sep. 1990.

PNEUMATIC SYSTEM

FIELD OF THE INVENTION

The invention relates generally to the field of respiratory assist devices and specifically to ventilators.

BACKGROUND OF THE INVENTION

Life support for patients with compromised respiratory function is commonly maintained by periodic introduction and extraction of a respiratory gas by mechanical means, such as a ventilator, through a tube inserted into the trachea of a patient. Introduction of the respiratory gas at a positive pressure causes the gas to move into and inflate the patient's lungs. After a predetermined time interval, the ventilator reduces the gas pressure and the patient's lungs deflate, causing the respiratory gas to be passively exhaled. Alternately pressurizing and depressurizing the patient's lungs with the respiratory gas, generally referred to as a ventilatory cycle, introduces oxygen into the lungs and removes carbon dioxide from the lungs which is necessary to keep the patient alive.

During the ventilatory cycle, various components of the ventilator are exposed to patient exhaled gases and can therefore be contaminated thereby. This poses a risk of cross-infection between successive patients treated with the ventilator. Given the extensive network of valves, tubes, and various chambers that are a part of a ventilator system, the challenge of sterilizing contaminated areas is daunting.

Although the risk of cross-infection is one problem to be overcome, it should be understood that other problems bear directly on the pneumatic performance of a ventilator. For example, rapid response to patient demand is highly desirable. Additionally, ventilators that provide gases for inspiration directly from a wall supply or a compressor must continuously feed the patient airway with gas from the supply source. This places a heavy demand on the gas source which can result in rapid depletion of gas supply. Worse yet, the demands of a patient or ventilator may exceed the capabilities of the supply sources.

SUMMARY OF THE INVENTION

A pneumatic system for a ventilator is provided that includes a computer controllable pneumatic circuit connectable to a disposable patient breathing circuit. The patient breathing circuit is configured to isolate exhaled patient gases from the pneumatic circuit to reduce the risk of cross-infection. The pneumatic system is adapted for computer control in association with a user interface for operation of the system and monitoring patient respiration.

In one embodiment, the pneumatic circuit includes a double venturi drive; a proportional control valve; an electronic gas blender; an integral humidifier; and integrated flow and pressure sensing equipment.

The disposable patient breathing circuit includes a bag reservoir to assist in delivering controlled pressure and flow wave forms to a patient in response to selected settings; an inspiratory tube; an exhaust tube; an exhaust valve; an exhaust flow transducer; and an exhaust check valve. A pressure sensor may be provided to measure pressure at the patient's airway.

The patient breathing circuit allows a patient to spontaneously breathe from the bag reservoir at any time, but allows the pneumatic circuit to deliver a control breath through the bag by pressurizing the canister that the bag resides in.

The patient breathing circuit provides significant advantages when compared to other ventilator circuits, namely, ease of spontaneously rebreathing by the patient; external gas mixing, allowing continuous blending of air and oxygen into the bag reservoir independent of the drive gas, for greater accuracy and better load control over a wide range of inspiratory flows; and allows controlled rebreathing and exhalation assist. Some of the dead space gases return to the bag reservoir, under the encouragement of a vacuum around the bag if desired, to reduce the effort the patient has to provide for exhaling their tidal volume.

BRIEF DESCRIPTION OF THE DRAWINGS

Other features and benefits of the invention can be more clearly understood with reference to the specification and the accompanying drawings in which.

DETAILED DESCRIPTION OF THE INVENTION

Figure 1:
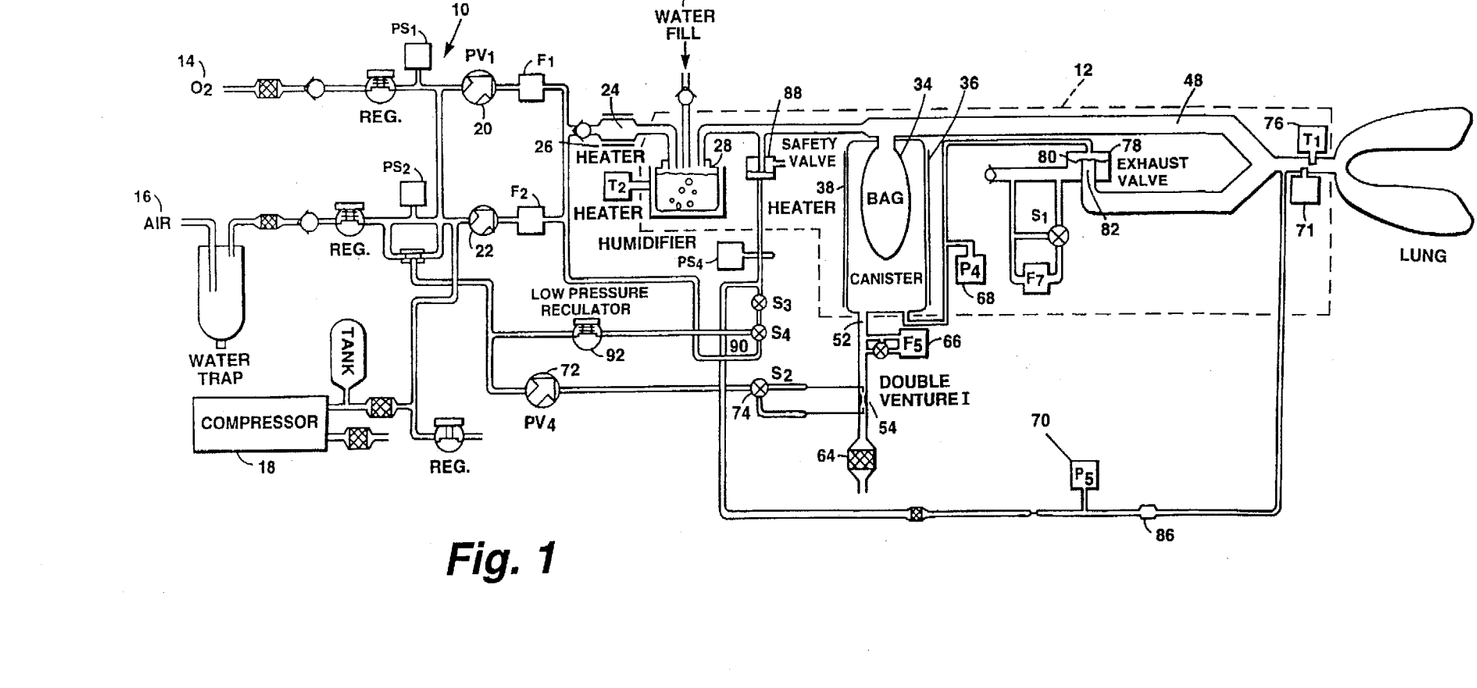
FIG. 1 is a schematic of the pneumatic system of the invention.

Referring to FIG. 1, the pneumatic system of the invention comprising a pneumatic circuit 10 and a disposable patient breathing circuit 12 is schematically illustrated. To more clearly segregate the elements of the circuits, FIG. 3 which illustrates only the elements of the disposable patient breathing circuit 12 should be referenced in association with FIG. 1.

Although the following description refers to control and operator inputs, a control unit, such as a computer; a user interface, such as a keyboard or touch screen; and control wires or lines from the control unit to various electromechanical devices such as valves or sensors are not shown as these features and their implementations are generally known in the art.

The pneumatic circuit 10 is shown connected to exemplary gas supplies such as a pure oxygen source 14, a "normal" air source 16, and a compressed gas source 18, via connectors known to those skilled in the art. The pneumatic system can be configured for connection to additional or fewer sources as needed. The features of the pneumatic system and an exemplary configuration thereof are described hereinbelow in association with the normal flow of gases through the pneumatic system.

Gasses provided by the sources 14, 16, and 18 enter the pneumatic circuit 10 and are blended by proportional flow control valves 20 and 22, to provide a blended mixture.

Continuous gas flow downstream from the control valve 20 and 22 towards a patient provides protection from external contaminants being introduced into the system through the patient breathing circuit 12. However, the protection can be enhanced by providing a zone or chamber 24 that can be heated by a heating device 26 to a temperature sufficient to permit heat sterilization, wherein the chamber is positioned downstream from the flow control valves 20 and 22.

Figure 5:
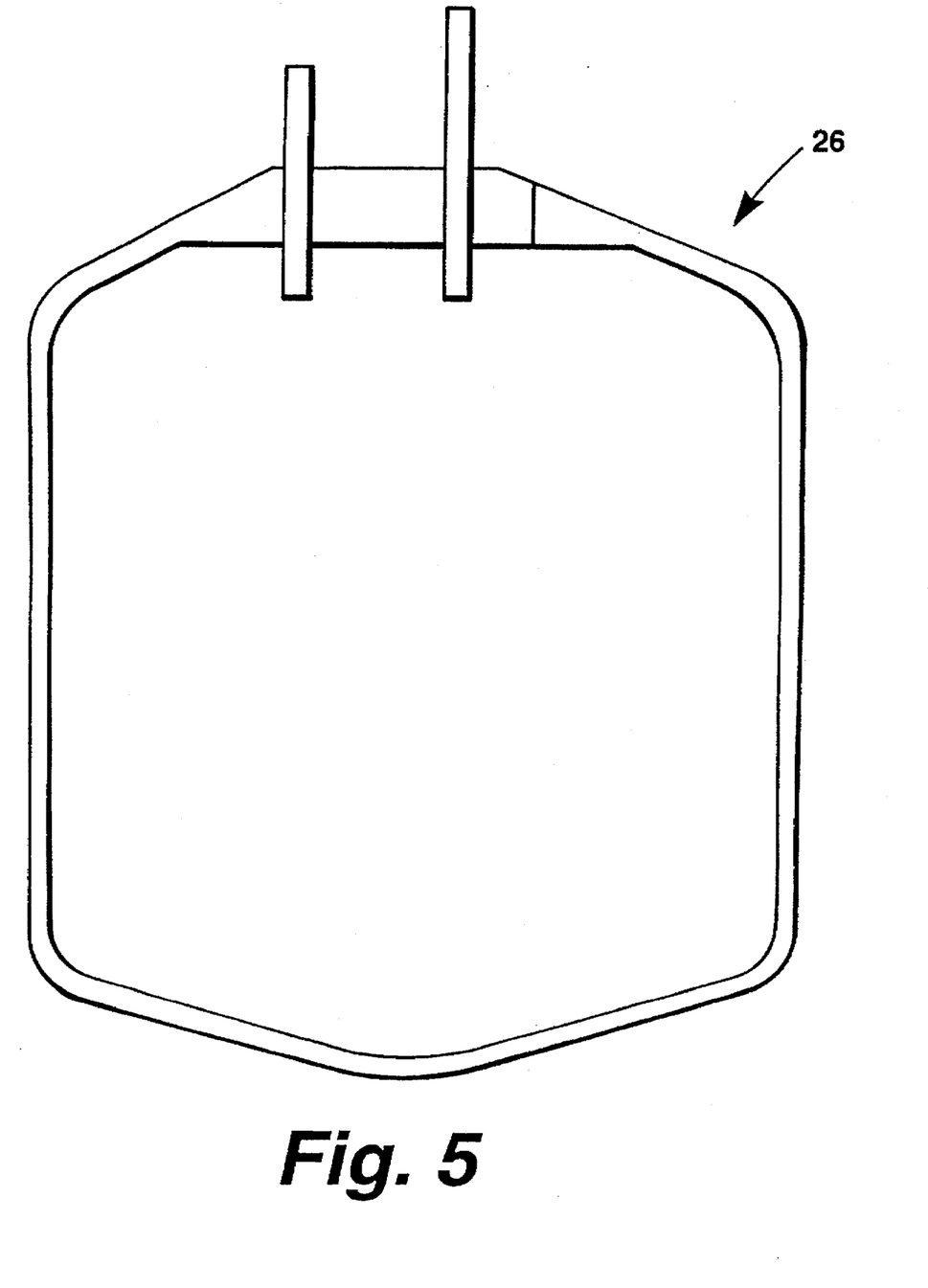
FIG. 5 is a sectional view of an exemplary humidifier of the invention.
Figure 6:
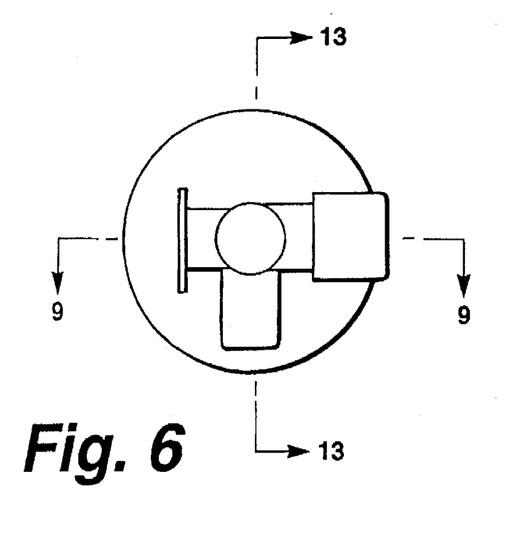
FIG. 6 is a top view of an exemplary canister manifold.
Figure 7:
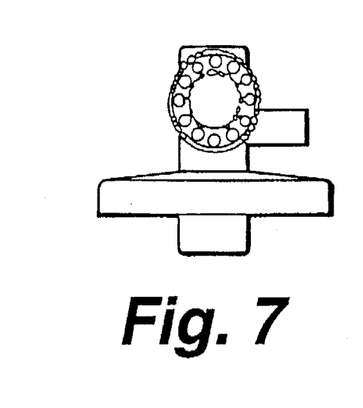
FIG. 7 is a side elevational view of the canister manifold of FIG. 6.
Figure 8:
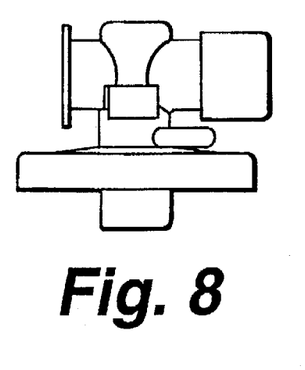
FIG. 8 is another side elevational view of the canister manifold of FIG. 6.
Figure 9:
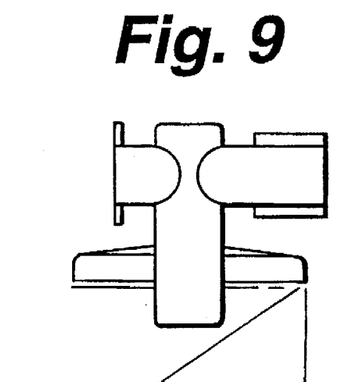
FIG. 9 is a sectional view of the canister manifold of FIG. 6 along the line 9—9.

Downstream from the control valves and the heatable chamber 24, a container 28 adapted to contain a liquid, such as water, is provided to humidify the blended mixture to provide a humidified mixture by passing it through or over the liquid. The container 28 can be automatically replenished with liquid as required through a fill port 30. A heater 32 maintains the liquid at an operator selectable temperature. In a typical application, dry supply gases are passed through the chamber 26 at a continuous flow rate of 3 to 20 liters per minute. Since this is a relatively constant flow of gas at low gas pressure, the container 26 can be of a relatively simple design and fabricated from inexpensive (i.e., disposable) material suitable for single patient use. FIG. 5 is an illustration of an exemplary container 26.

The humidified mixture is conducted from the container 28 into a flexible bag or reservoir 34 that is part of the patient breathing circuit 12. The reservoir 34, intended for single patient use, can be fabricated from a thin-walled elastomeric material or a flexible plastic. An exemplary reservoir is fabricated from a 0.007 inch thick sheet of polyvinyl chloride (PVC), capable of withstanding pressure of 2 pounds per square inch and temperatures in excess of 180° degrees Fahrenheit.

In the illustrated embodiment, the flexible reservoir 34 is positioned within a sealed, rigid canister 36. A heat source 38 can be associated with the canister 36 to warm the flexible reservoir 34 to aid in delivering heat and humidity gases in the patient breathing circuit 12. Heating the flexible reservoir 34 also prevents accumulation of condensation from rebreathed patient gases by revaporizing the condensate, thus reducing the need for additional humidity by a supplemental humidifier. An exemplary heat source 38 includes a thermal blanket wrapped around a portion of the canister 36. The heat source 38 is responsive to a temperature sensor 76 which monitors the temperature of the gases delivered to the patient.

Figure 4:
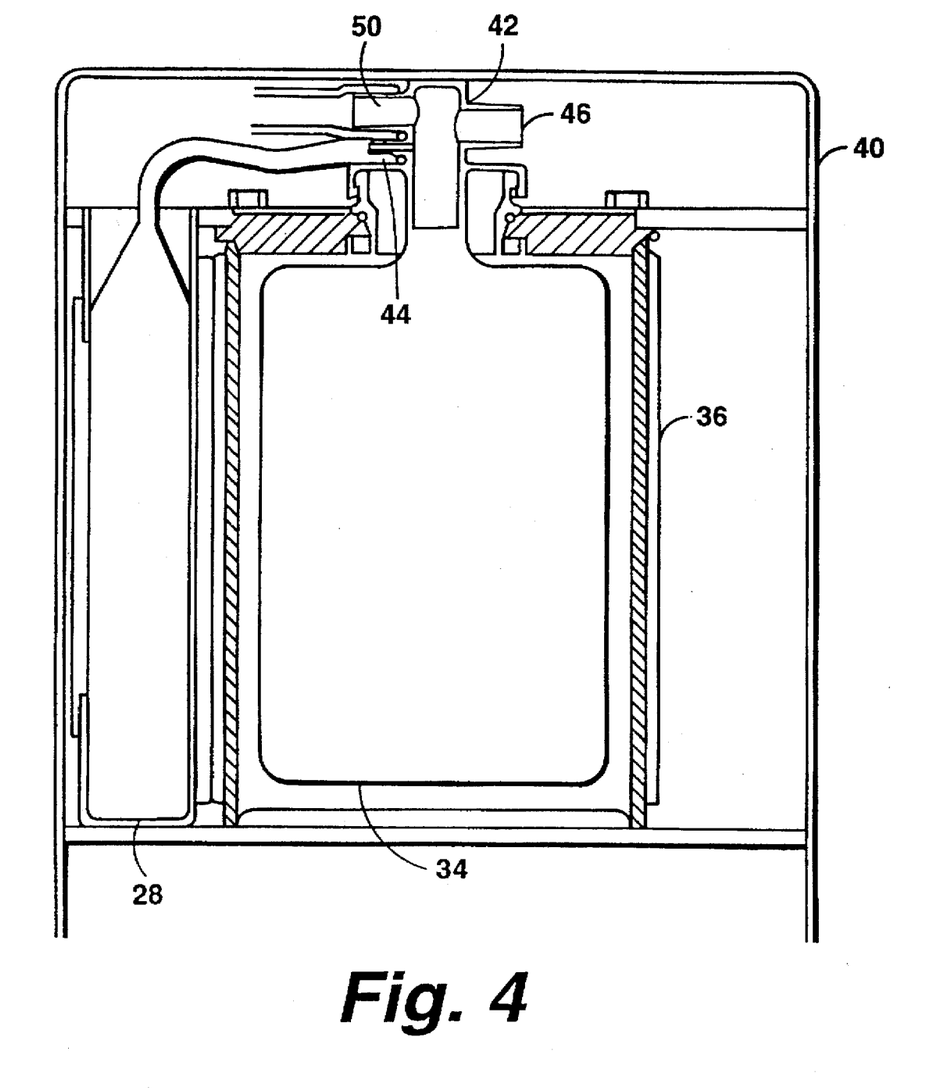
FIG. 4 is a sectional view of an exemplary canister, flexible reservoir, and humidifier of the invention.

FIG. 4 is a sectional illustration of an exemplary configuration of the flexible reservoir 34, the canister 36, and the container 28 secured within a housing 40. The flexible reservoir is shown in a removably sealed relationship with a manifold 42 and the manifold is removably sealed to the canister 36.

Figure 10:
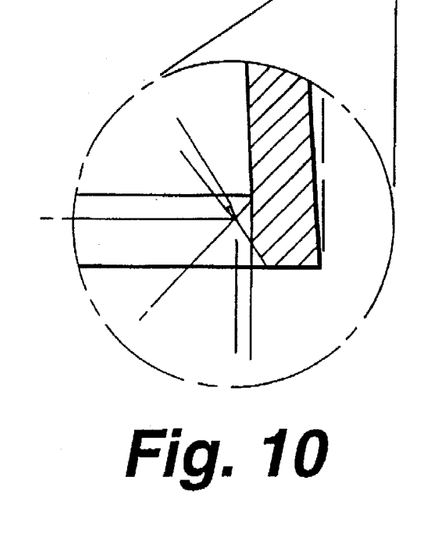
FIG. 10 is a detail view of a portion of the canister manifold of FIG. 9.
Figure 11:
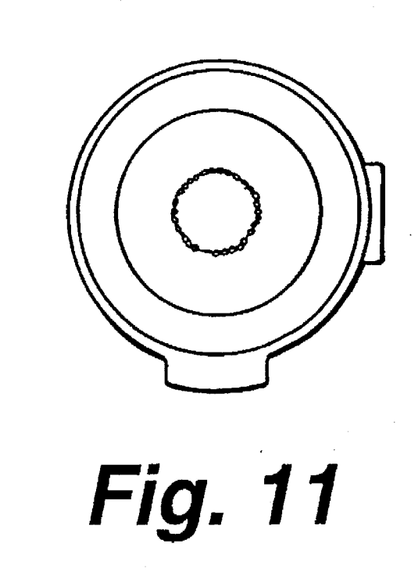
FIG. 11 is bottom view of the canister manifold of FIG. 6.
Figure 12:
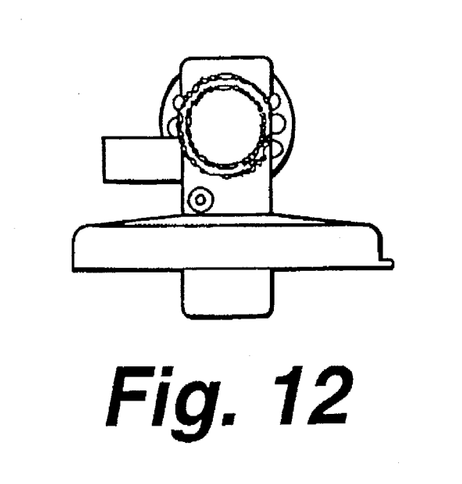
FIG. 12 is another side elevational view of the canister manifold of FIG. 6.
Figure 13:
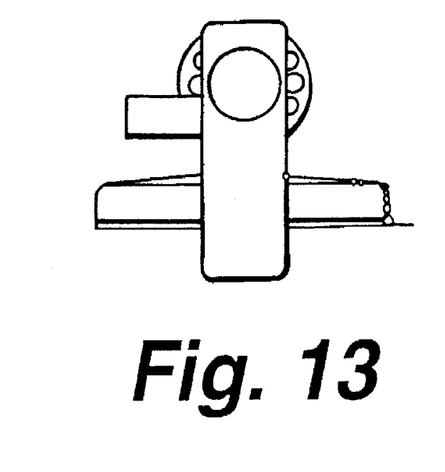
FIG. 13 is a sectional view of the canister manifold of FIG. 6 along the line 13—13.

FIGS. 6–13 show details of the manifold 42 from different angles and cross-sections. FIG. 10 is a detailed view of a lip which mates with a complimentary surface to secure the manifold 42 in place.

Referring to FIG. 4, it should be noted that the manifold 42 includes a first port 44 for connection to the container 28, a second port 46 for connection to an airway 48 (see FIGS. 1 and 3) leading toward the patient, and a third port 50 for connection to an exhaust port described below.

Figure 2:
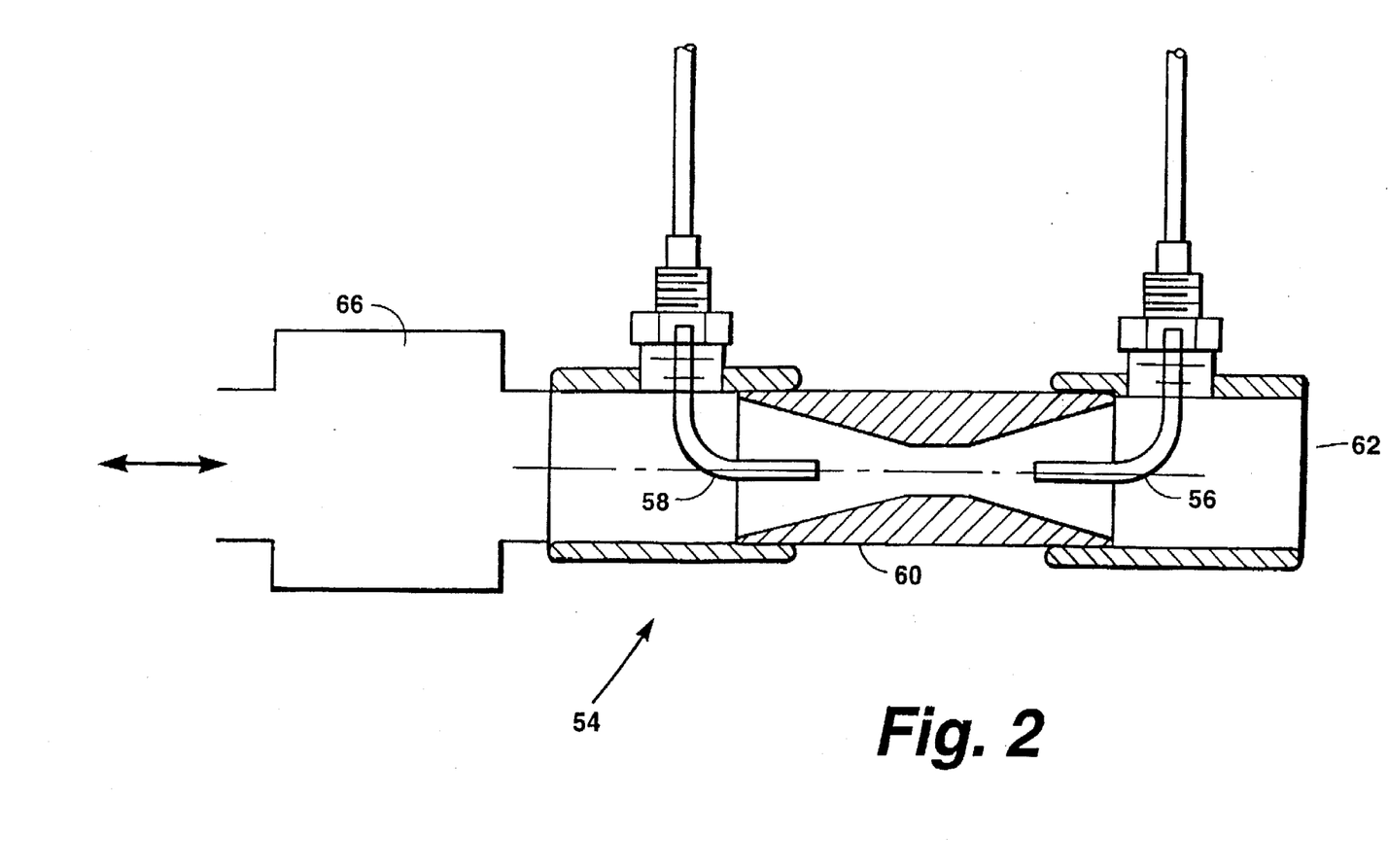
FIG. 2 is a sectional view of the double venturi illustrated in FIG. 1.

The canister has a port 52 through which a gas may flow bi-directionally to and from the interior of the canister 36. A dual or double venturi 54 communicates with the interior of the canister 36 through the port 52. FIG. 2 illustrates the double venturi 54 in greater detail, wherein first and second jet tubes 56 and 58 are positioned with their outlets directed toward a throat 60 and are on opposite sides of the throat. Gas expelled from the first jet tube 56 entrains room air entering through a port 62 which can be provided with a filter 64 (see FIG. 1), and directs the air through the port and into the canister 36 to provide a compressive force to the exterior of the flexible reservoir 34. By contrast, gas expelled from the second jet tube 58 entrains gas in the canister 36 and directs it through the port 62 to reduce the pressure within the canister and thereby on the flexible reservoir 34. Thus, as the pressure in the canister 36 affects the pressure applied to the flexible reservoir 34, the flow to or from the patient is affected.

The double venturi 54, which can induce sub-ambient pressure conditions within the canister 36, serves as an expiratory assist device that allows faster completion of the exhalation phase of the total breathing cycle of the patient, allowing the next inhalation cycle to start earlier than if only elastic recoil of the lungs were used to complete exhalation. This allows faster breath rates for improved therapy in both oxygenation of the lung and removal of $CO_2$. This also allows the use of smaller tidal volumes, lower inspiratory pressures, and lower average airway pressures.

In the illustrated embodiment as shown in FIG. 2, a flow transducer 66 is placed between the double venturi 54 and the canister 36 to measure flow to and from the canister. A signal output from the flow transducer 66 can be used to calculate the volume of gas delivered to the patient's lungs.

Referring again to FIG. 1, a pressure transducer 68 in communication with the interior of the canister 36 can be provided to measure the pressure within the canister. A second pressure transducer 70 can be provided to measure the pressure of gas delivered to the patient's lungs. By comparing the signals of the first and second pressure transducers 68 and 70, respectively, the integrity of the system and verification of operating pressure can be monitored.

Control of the pressure within the canister 36 is effected by actuation of a proportional flow valve 72 which can provide a variable flow of gas to a three way valve 74 which is positionable to direct the flow of gas to either or neither of the first and second jet tubes 56 and 58, respectively. Thus, patient airway flow and pressure can be controlled in both inspiratory and expiratory phases by a single proportional flow valve 72, such as a solenoid. It should be noted that the mixture of gases delivered to the patient can be different from the gas passing through the proportional flow valve 72. For example, the double venturi 54 can be operated with normal air while the patient is provided with pure oxygen.

In addition to the above described features, it should be noted that the combination of the double venturi 54 driven by a proportional valve 72 permits a rapid onset of high flow when the proportional valve is actuated. This is achieved by requiring only a fraction of the necessary total flow into the breathing circuit 12 to be supplied to the selected venturi jet tube, as the majority of flow is achieved by entrainment of surrounding air when the jet flow is initiated. Since both flows initiate at the same time, a small flow from the jet results in a large flow to the patient at a response time determined by the proportional valve driving only the jet.

Since the jet requires a smaller flow than is supplied at the venturi outlet, only a relatively small and therefore fast to respond valve is required.

Control signals for actuating the proportional flow valve 72 can originate from the pressure transducer 68 in a feedback control loop or from an optional proximal flow transducer 71 which can be used to monitor the patient's inspiratory and expiratory volume. Thus, either pressure or flow signals can be used to control the proportional flow valve 54.

An exhalation or exhaust valve 78 permits gases to be expelled from the patient breathing circuit 12. The valve 78 can comprise a diaphragm 80 and a seat 82. One side of the diaphragm 80 is in communication with interior of the canister 36 so as to be responsive to the pressure within the canister. When pressure is elevated in the canister 36, such as during the beginning of an inspiratory phase, the diaphragm 80 is pushed against the seat 82, thereby closing the exhaust valve 78 for the duration of inspiration. When the inspiratory phase is completed, the pressure in the canister 36 drops or is caused to drop, thereby relieving pressure on the diaphragm 80 and allowing gas to exit the exhaust valve 78. In one embodiment of the pneumatic system, the exhaust valve 58 requires a bias pressure of about 2 cm $H_2O$ to assure the flexible reservoir 34 is reinflated before the exhaust valve 78 opens.

In a typical application, the first portion of a patient's exhalation which is not used for gas exchange in the lungs returns to the flexible reservoir 34, but as the flexible reservoir fills, the later portion of the exhalation which has been used for gas exchange is released through the exhaust valve 78.

Another feature of the exhaust valve 78 is that it maintains the patient airway pressure at an elevated level to keep small airways in the lung open in certain lung therapies, called PEEP (Positive End Expiratory Pressure). PEEP is achieved in the pneumatic system by applying a continuous pressure to the canister 36 during the expiratory phase with the double venturi 54 caused to be responsive to a pressure feedback control signal from the canister pressure transducer 68 or the patient airway pressure transducer 70. By supplying pressure to the canister 36 and the exhaust valve 78 simultaneously, an elevated pressure above ambient pressure can be maintained under a no-flow condition. Because the proportional flow valve 72 already controls flow and pressure via the double venturi 54 during the inspiratory phase, the servo-controlled PEEP function is achieved without adding to the complexity or cost of the system.

As described above, the flexible reservoir 34 fills with a controlled portion of the gas exhaled by a patient to provide a rebreathing reservoir to supplement one or more of the gas sources 14, 16, 18. In addition to improving gas utilization by reusing dead space gases that were not used in gas exchange in the lungs, the rebreathing reservoir 34 allows partial rebreathing to adjust patient arterial $CO_2$ levels when desired.

The amount of patient exhaled gas that is rebreathed is regulated by the amount of incoming gas supplied through the supply gas flow control valves 20, 22 which can be electronically controlled using signals from a gas sampling array 84 (see FIG. 3) that measures inspired and/or expired $CO_2$ levels to provide a desired level of rebreathing, thus providing independent control of $CO_2$ elimination and oxygenation of the patient's lungs. The gas mixture can be further modified by adjusting the supply flow control valves 20, 22.

Another advantage provided by the illustrated configurations in comparison with a conventional direct-drive ventilator is that the present invention allows the flow control valves 20, 22 to supply gas to the pneumatic system continuously, rather than intermittently, such that demand flow from a hospital wall outlet, air compressor, gas concentrator, or pressurized gas bottle, for example is lower and is less likely to cause large pressure fluctuations that can affect accuracy of delivered volumes and concentrations.

Additionally, the flexible reservoir 34 of the invention makes available to the patient a volume of the blended humidified mixture which reduces the effort required to initiate a breath by the patient. When the patient initiates a breath, the volume of gas in the reservoir is reduced, which is sensed by the flow transducer 66 and the breath is augmented as desired by the clinician. This volume trigger reduces the overall work of breathing provided by the patient, reducing patient fatigue and reduces the likelihood of inadvertent triggers. Similarly, when the patient begins to exhale, the exhaled gas increases the pressure in the volume in the flexible reservoir 34 without increasing pressure in the patient airway which is sensed by the flow transducer 66. Since the patient can maintain control of the respiratory cycle with less effort, there is better retention of the patient's respiratory drive under mechanical ventilation.

Yet another feature of the flexible reservoir 34 is that it permits introduction of special gas mixes containing low percentages of measurement gases. In one embodiment, an additional gas source provides the special gas mixture which would be introduced into the system upstream of chamber 24. The concentrations of these trace gases in the patient's airway are measured by the gas sampling array 84.

The flexible reservoir 34 also facilitates dilute gas equilibration techniques using the gas mixture as just described. In one example, an inert gas such as methane or helium, used for measurement of functional residual capacity or total lung volume, completely fills the flexible reservoir 34. The patient rebreathes the inert gas until an equilibrium point is reached. This rebreathing capability allows an assessment of the quality of ventilation and lung function while the patient remains on the ventilator. By contrast, conventional ventilators require the patient to be disconnected from the ventilator and transported to a specialized pulmonary function laboratory for this type of testing, which is generally not clinically feasible.

The flexible reservoir can also be used to totally rebreathe a mixture of special gases, such as acetylene, that can be used for assessment of pulmonary blood flow by measuring the reduction in concentration as it is absorbed in the bloodstream. This test can occur while the patient is attached to the pneumatic system by filling the flexible reservoir 34 with a known concentration of these gases and totally rebreathing this mixture by shutting off the supply of gases from the blended source until a point of equilibrium is reached.

Referring again to FIGS. 1 and 3, the patient airway pressure transducer 70 is protected from patient exhalation by an in-line filter 86 and by continuous flow of gas from the pneumatic circuit towards the patient breathing circuit outlet. Location of the pressure and flow measurement transducers 70 and 71, respectively, can be in several parts of the circuit to be effective. In one embodiment, the patient airway pressure transducer 70 provides a signal output that can be used to regulate the gas flow from the proportional flow valve 72 to maintain a desired patient airway pressure. Addition verification is possible by comparing an output signal from the canister pressure transducer 68 with an output signal from the patient airway pressure transducer 70. The patient airway pressure transducer 70 can also monitor the pneumatic system and activate a safety valve 88 to relieve the patient breathing circuit pressure if a fault is detected. The safety valve 88 is normally held closed by a safety solenoid valve 90 which is supplied pressure by a low pressure regulator 92.

Figure 3:
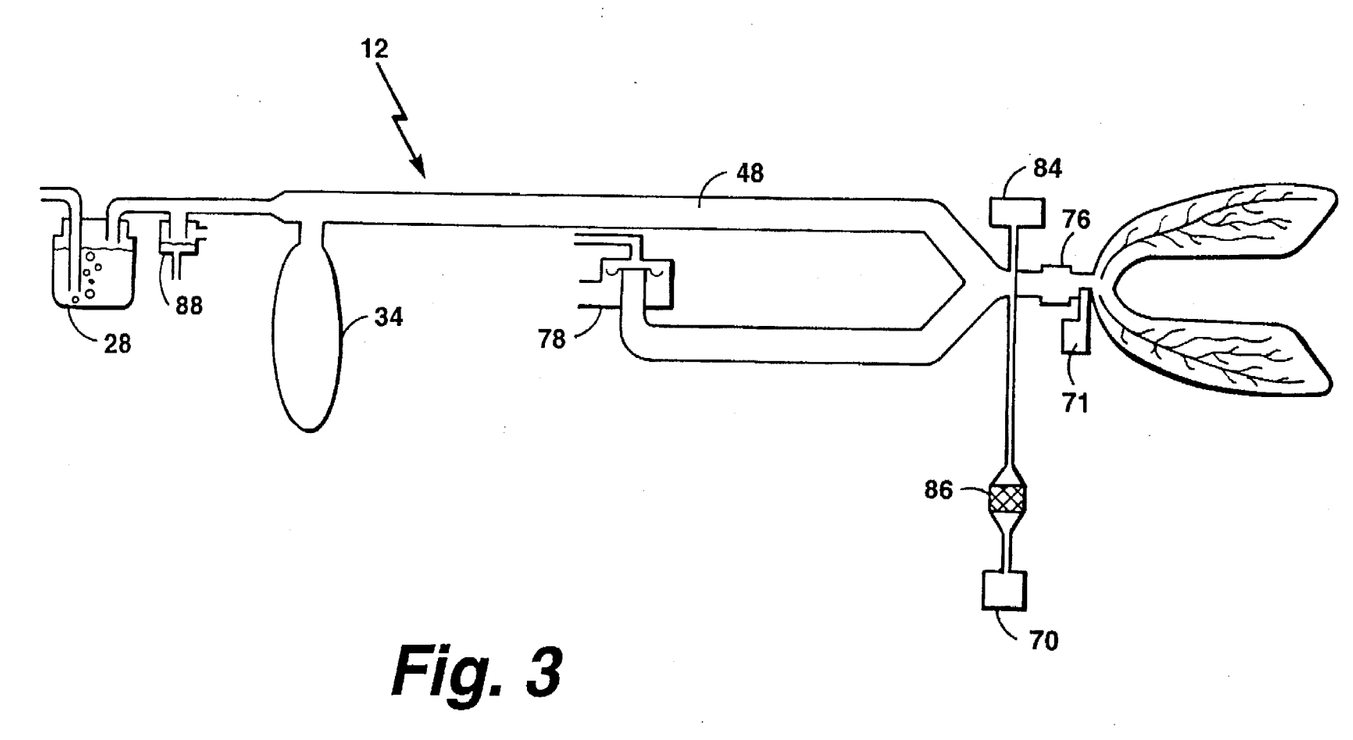
FIG. 3 is a schematic illustration of an embodiment of the disposable patient breathing circuit of FIG. 1.

Although the it should be understood that the retention of patient gases in the patient breathing circuit 12 yields benefits, the risk of cross-infection might outweigh those benefits were not the patient breathing circuit 12 disposable. To this end, all of the components that come in contact with the patient's exhaled gases are easily detachable from the pneumatic circuit 10 as illustrated in FIG. 3. Therefore, the exhaust valve 78 and the patient safety valve 88 can also be part of the disposable patient breathing circuit 12 to minimize cross contamination.

Although the invention as been shown and described with respect to exemplary embodiments thereof, various other changes, omissions and additions in form and detail thereof may be made therein without departing from the spirit and scope of the invention.

What is claimed is:

1. A pneumatic system for a ventilator in fluid communication with a source of gas comprising:
    a pneumatic circuit including a sealed canister, a valve, a double venturi having first and second jets and a proportional control valve for providing a selected volume of said gas to said valve, said valve directing said gas to one of said first jet and said second jet of said double venturi, said double venturi being in fluid communication with said sealed canister; and
    a patient breathing circuit including a first port for introducing said gas into said patient breathing circuit, a humidifier downstream from said source of gas for humidifying said gas, a flexible reservoir for containing a variable volume of said gas, said flexible reservoir located within said sealed canister downstream from said humidifier, and a second port downstream from said flexible reservoir,
    wherein gas directed through said first jet entrains gas within said sealed canister away from said sealed canister to reduce the pressure on the exterior of said flexible reservoir, and gas directed through said second jet entrains gas toward said sealed canister to increase pressure on the exterior of said flexible reservoir.

2. The pneumatic system of claim 1, further including a sterilization chamber through which said gas is passed and a heating device for heating said sterilization chamber, said sterilization chamber located upstream from said patient breathing circuit.

3. The pneumatic system of claim 1, further including a heater responsive to system operator control for maintaining a fluid in said humidifier at a selectable temperature.

4. The pneumatic system of claim 1, further including a manifold connectable to said flexible reservoir and said humidifier, said manifold removably sealing said flexible reservoir within said canister to define a zone between the interior of said canister and the exterior of said flexible reservoir, said zone being in fluid communication with said double venturi.

5. The pneumatic system of claim 4, further including an exhaust port and an airway between said manifold and said second port, wherein said manifold provides a fluid connection to said humidifier, said flexible reservoir, said airway, and said exhaust port.

6. The pneumatic system of claim 4, further including a first pressure transducer in fluid communication with said zone and a second pressure transducer proximate said second port.

7. The pneumatic system of claim 4, further including an exhaust valve in fluid communication with said zone in said canister and a gas flow downstream from said flexible reservoir, said exhaust valve being in a closed state until a predetermined pressure is achieved within said flexible reservoir.

8. The pneumatic system of claim 1, further including a heat source associated with said sealed canister to warm said flexible reservoir.

9. The pneumatic system of claim 8, wherein said heat source includes a thermal blanket wrapped around a portion of said canister.

10. The pneumatic system of claim 8, further including a temperature sensor that monitors the temperature of said gas downstream from said flexible reservoir to provide a control signal to said heat source.

11. The pneumatic system of claim 1, further including a flow transducer for measuring gas flow to and from said canister.

12. The pneumatic system of claim 1, further including a gas sampling array proximate said second port and a plurality of gas flow control valves in fluid communication with said first port of said patient breathing circuit and respective sources of gas, said gas sampling array providing an output signal to which said plurality of gas flow control valves are responsive.

13. A pneumatic system for a ventilator in fluid communication with a source of gas comprising:
    a canister;
    a flexible reservoir within said canister;
    a manifold in fluid communication with said flexible reservoir, said manifold removably sealing said flexible reservoir within said canister to define a zone between the interior of said canister and the exterior of said flexible reservoir;
    a heat source associated with said sealed canister to warm said flexible reservoir;
    an airway in fluid communication with said flexible reservoir;
    a gas flow control valve in communication with said source of gas;
    a sterilization chamber downstream from said gas flow control valve through which a portion of said gas is passed to provide a heat sterilized gas;
    a heating device for heating said sterilization chamber;
    a humidifier downstream from said gas flow control valve for humidifying said sterilized gas, said humidifier in fluid communication with said flexible reservoir;
    a heater heating a fluid in said humidifier;
    a proportional control valve for providing a selected volume of said gas from said gas flow control valve;
    a double venturi having a first jet and a second jet for entraining gas in opposite directions through said double venturi, said double venturi in fluid communication with said zone in said canister; and
    a venturi control valve directing said gas provided by said proportional control valve to one of said first jet and said second jet, wherein gas directed through said first jet entrains gas within said sealed canister away from said sealed canister to reduce the pressure on the exterior of said flexible reservoir, and gas directed through said second jet entrains gas toward said sealed canister to increase pressure on the exterior of said flexible reservoir.

14. A pneumatic system for a ventilator in fluid communication with a source of gas comprising:

a canister;

a flexible reservoir within said canister;

a manifold in fluid communication with said flexible reservoir, said manifold removably sealing said flexible reservoir within said canister to define a zone between the interior of said canister and the exterior of said flexible reservoir;

a heat source associated with said sealed canister to warm said flexible reservoir;

an airway in fluid communication with said flexible reservoir;

a gas flow control valve in communication with said source of gas;

a sterilization chamber downstream from said gas flow control valve through which a portion of said gas is passed to provide a heat sterilized gas;

a heating device for heating said sterilization chamber;

a humidifier downstream from said gas flow control valve for humidifying said sterilized gas to provide humidified, sterilized gas, said humidifier in fluid communication with said flexible reservoir;

a heater heating a fluid in said humidifier;

a temperature sensor in said airway that monitors the temperature of said humidified, sterilized gas to provide a control signal to said heat source;

a proportional control valve for providing a selected volume of said gas from said gas flow control valve;

a double venturi having a first jet and a second jet for entraining gas in opposite directions through said double venturi, said double venturi in fluid communication with said zone in said canister;

a venturi control valve directing said gas provided by said proportional control valve to one of said first jet and said second jet, wherein gas directed through said first jet entrains gas within said sealed canister away from said sealed canister to reduce the pressure on the exterior of said flexible reservoir, and gas directed through said second jet entrains gas toward said sealed canister to increase pressure on the exterior of said flexible reservoir;

an exhaust valve in fluid communication with said zone in said canister and said airway;

a flow transducer for measuring gas flow to and from said canister;

a first pressure transducer in fluid communication with said zone and a second pressure transducer in fluid communication with said airway; and a gas sampling array in fluid communication with said airway, said gas sampling array providing an output signal to which said gas flow control valve is responsive.

\* \* \* \* \*